US011439516B2

(12) United States Patent
Tavani et al.

(10) Patent No.: US 11,439,516 B2
(45) Date of Patent: Sep. 13, 2022

(54) IMPLANT WITH FREELY MOVEABLE ENDPLATES

(71) Applicant: K2M, Inc., Leesburg, VA (US)

(72) Inventors: Daniel Tavani, Duluth, GA (US); Michael Schular, Gainesville, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 17/205,137

(22) Filed: Mar. 18, 2021

(65) Prior Publication Data

US 2021/0290405 A1 Sep. 23, 2021

Related U.S. Application Data

(60) Provisional application No. 62/991,943, filed on Mar. 19, 2020.

(51) Int. Cl.
*A61F 2/44* (2006.01)
*A61F 2/30* (2006.01)

(52) U.S. Cl.
CPC ............ *A61F 2/446* (2013.01); *A61F 2/4425* (2013.01); *A61F 2002/30492* (2013.01); *A61F 2002/443* (2013.01)

(58) Field of Classification Search
CPC .. A61F 2/442; A61F 2/4425; A61F 2002/443; A61F 2002/30492; A61F 2002/4445; A61F 2002/445; A61F 2/4455
USPC ............................................ 623/17.11–17.16
See application file for complete search history.

(56) References Cited

U.S. PATENT DOCUMENTS

| 6,176,882 B1 * | 1/2001 | Biedermann | A61F 2/447 623/17.11 |
| 10,369,008 B2 * | 8/2019 | Jimenez | A61B 17/7065 |
| 2017/0231781 A1 | 8/2017 | Kraemer | |
| 2017/0367842 A1 * | 12/2017 | Predick | A61F 2/4455 |

FOREIGN PATENT DOCUMENTS

WO    2017048886 A1    3/2017

OTHER PUBLICATIONS

Dr. Neckrysh, "Spherical Disc" Drawings; Dated Feb. 4, 2015; 1page.

* cited by examiner

*Primary Examiner* — Eduardo C Robert
*Assistant Examiner* — Christina NegrelliRodriguez
(74) *Attorney, Agent, or Firm* — Lerner, David, Littenberg, Krumholz & Mentlik, LLP

(57) ABSTRACT

An interbody fusion device including pivoting endplates is disclosed. The endplates define grooves between the endplates to house sliding pins. A threaded shaft extends through the implant to connect the endplates and the sliding pins. The implant is fit to be inserted into an intervertebral disc space to pivot according to the natural angles of the adjacent vertebrae. The shaft can be rotated to adjust the sliding pins into a position to provide support to the endplates at the angle they take between the vertebrae.

20 Claims, 12 Drawing Sheets

IMPLANT WITH FREELY MOVEABLE ENDPLATES

CROSS-REFERENCE TO RELATED APPLICATIONS

This application claims the benefit of the filing date of U.S. Provisional Patent Application No. 62/991,943 filed Mar. 19, 2020, the disclosure of which is hereby incorporated herein by reference.

BACKGROUND OF THE INVENTION

The present invention relates to spinal surgery, namely, the fusion of adjacent intervertebral bodies.

Back pain can be caused by many different maladies, not the least of which are problems that directly impact the intervertebral discs of the spine and overall motion segment. In particular, Idiopathic Scoliosis can cause vertebral body wedging in conjunction with coronal deformity. One method of treatment of such a disc problem is to place large lateral cages across the interbody space to correct the coronal curve. When placed, the endplates of the implants should provide maximum contact with the vertebral bodies to support loading and ultimately fusion, but this is not always the case. One issue is that some of the vertebrae, commonly at the apex of the curve, are or become wedged in shape. Thus, achieving the maximum contact between the implant and the vertebral bodies often requires an implant that has the ability to match that wedge shape and lock into place.

Currently, static cages with a coronal taper are used to match the vertebral wedging while aiding the correction of the coronal deformity. These require impaction into the disc space and are offered in one or two tapered size options. This does not always provide a precise match of the endplates, and it requires a wide variety of cages to be held in inventory. While these static cages often come in multiple footprints, heights, and wedge angles, they are often not an optimum fit for precise matching for all patients and surgical situations or are dependent on trialing.

Therefore, there exists a need for an improved spinal implant that overcomes the aforementioned drawbacks while improving efficiency of the overall procedure.

SUMMARY OF THE INVENTION

The present invention provides a unique design that allows a pivoting cage to more precisely match any shape within the cage's designed range. The implant is inserted laterally through the patient into the intervertebral space. After insertion, the implant will settle into the shape of the vertebrae. A surgeon can then wield a tool to lock the cage in place, which will prevent further pivoting and provide support for the surrounding vertebral bodies.

The pivoting cage is a passive device, which means the load on the disc space will adjust the implant, rather than a forced expansion applied by a surgeon, which potentially provides better matching of the wedged anatomy. Providing a wider range of angles than a fixed static cage also provides a more efficient implant selection in the operating room, as well as benefits related to inventory management.

In certain preferred embodiments, the pivoting cage may comprise a first endplate, a second endplate pivotally coupled to the first endplate, a first sliding pin slidably disposed between the first and second endplates adjacent a first end of the implant, a second sliding pin slidably disposed between the first and second endplates adjacent a second end of the implant, and a shaft extending at least partially through the first and second sliding pins, wherein actuation of the shaft locks the first and second endplates with respect to each other. The first endplate may define a bore in which the shaft extends therethrough. The first endplate may define a first groove configured to receive the first sliding pin. The first sliding pin may define a bore configured to receive the shaft. The bore of the first sliding pin may be threaded. The first endplate may define a second groove configured to receive a second sliding pin, and the second sliding pin may define a bore configured to receive the shaft. The second endplate may define a first tapered slot configured to receive the first sliding pin. The second endplate may further define a second tapered slot configured to receive the second sliding pin. The first and second endplates may be pivotally coupled to each other by at least one pivot pin. The pivot pin may be located at a center of the implant and extend orthogonal to a longitudinal axis of the implant. The first endplate may lie in a first plane and the second endplate may lie in a second plane parallel to the first plane. The first endplate may lie in a first plane and the second endplate may lie in a second plane that intersects with the first plane. The shaft may be at least partially threaded. The second sliding pin may further define a hole configured to receive a locking pin that extends through the second sliding pin and within a circumferential indentation in the shaft to prevent the shaft from translating relative to the second sliding pin but allowing rotation of the shaft. The shaft may include a drive feature configured to receive a tool for rotating the shaft. A clockwise rotation of the shaft may cause the first sliding pin to translate along the shaft axis in a direction away from the second sliding pin. The first and second endplates may have bullet-shaped ends.

In other embodiments of the disclosure, an intervertebral implant may include a first endplate, a second endplate and a first sliding pin. The first endplate may extend along a longitudinal axis. The first endplate may define a groove. The second endplate may be pivotally coupled to the first endplate. The second endplate may define a tapered slot which may align with the groove of the first endplate along the longitudinal axis when the implant is in an assembled configuration. The first sliding pin may be slidably disposed within the groove and the tapered slot. Movement of the sliding pin along the longitudinal axis may pivot the second endplate relative to the first endplate. The implant may further include a shaft extending between the first and second endplates along the longitudinal axis. The shaft may pass through the sliding pin. The shaft may be configured to translate the sliding pin along the longitudinal axis.

A method of positioning the interbody fusion device may comprise inserting an implant between first and second vertebral bodies, the implant including a first endplate for contacting the first vertebral body and a second endplate for contacting the second vertebral body; allowing the first and second endplates to freely pivot with respect to each other to conform to the angle between the two adjacent vertebrae; and actuating a shaft of the implant to lock the first and second endplates with respect to each other. The inserting step may include inserting the implant laterally through the patient. The actuating step may include translating a first and second sliding pin until the first and second sliding pins meet resistance between the first and second endplates. During the inserting step, the first and second sliding pins may be positioned medially to allow the implant to pivot into the natural state of the vertebrae.

DETAILED DESCRIPTION

As used herein, the term "proximal," when used in connection with an implant or components of an implant, refers to the end of the device closer to the user of the device when the device is being used as intended. On the other hand, the term "distal," when used in connection with an implant or components of an implant, refers to the end of the device farther away from the user when the device is being used as intended. As used herein, the term "substantially" is intended to mean that slight deviations from absolute are included within the scope of the term so modified.

Figure 1:
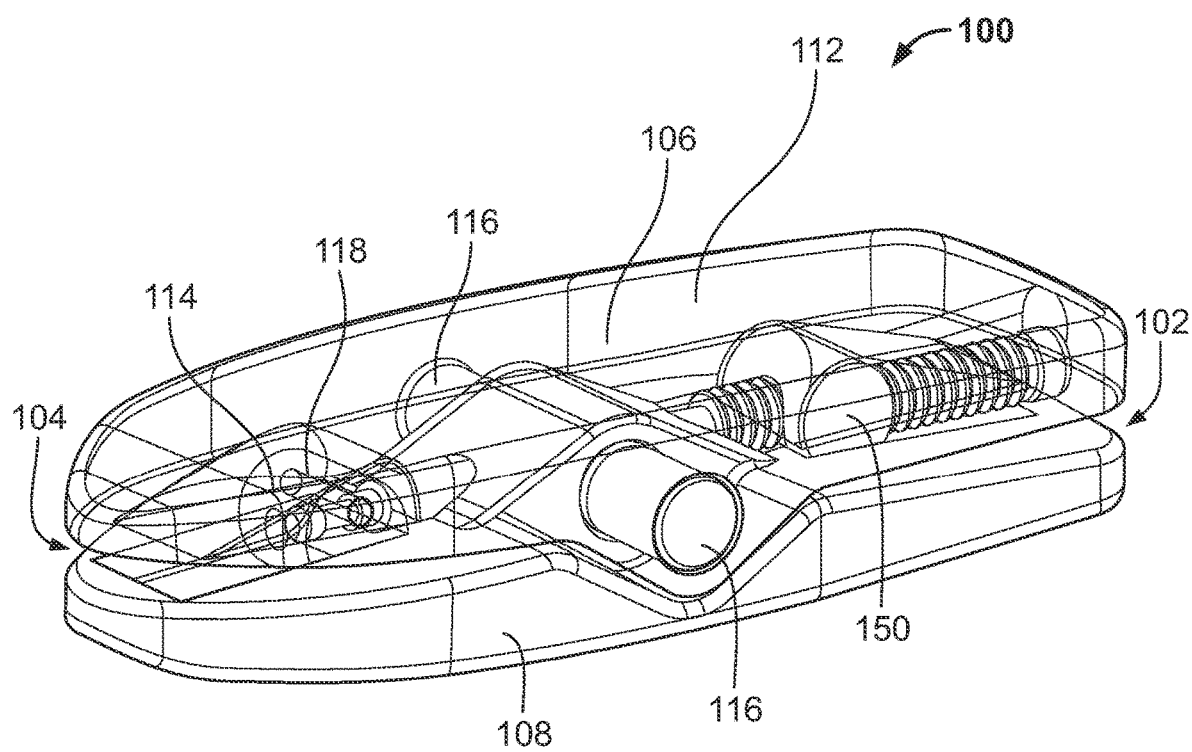
FIG. 1 is a perspective partial cross-sectional view of an implant according to one embodiment of the present invention.
Figure 2:
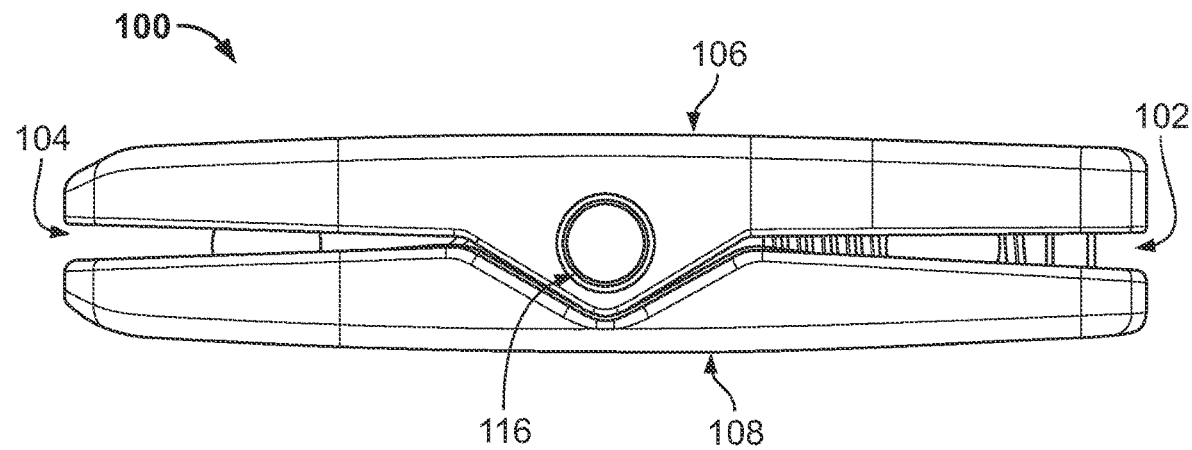
FIG. 2 is a side view of the implant of FIG. 1.

As shown in FIG. 1, implant 100 includes proximal end 102 and distal end 104, as well as top endplate 106 and bottom endplate 108 connected by pivot pins 116. Endplates 106, 108 may be 3D printed so that they exhibit porous and/or solid portions, such as are included in the various Tritanium and Cascadia implants offered by Stryker Spine and/or K2M, Inc. Endplates 106, 108 are shown with bulleted noses at distal end 104, which can be useful in inserting implant 100 between vertebral bodies. In other embodiments, different shaped noses can be employed. End plates 106, 108 are shown exhibiting a shape in which their lengths are substantially longer than their widths. This can vary depending upon the particular use for implant 100. It is contemplated to construct the end plates and other components (discussed below) of various suitable materials, including, but not limited to, titanium, stainless steel or the like.

Figure 3:
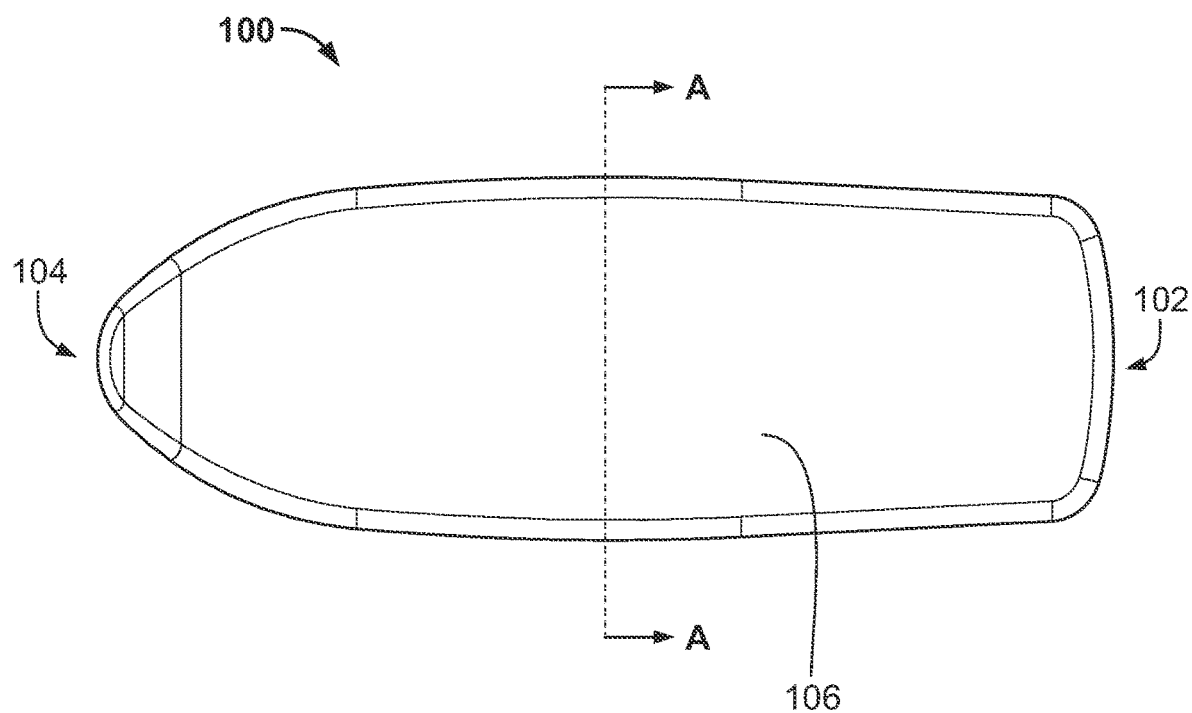
FIG. 3 is a top view of the implant of FIG. 1.
Figure 4:
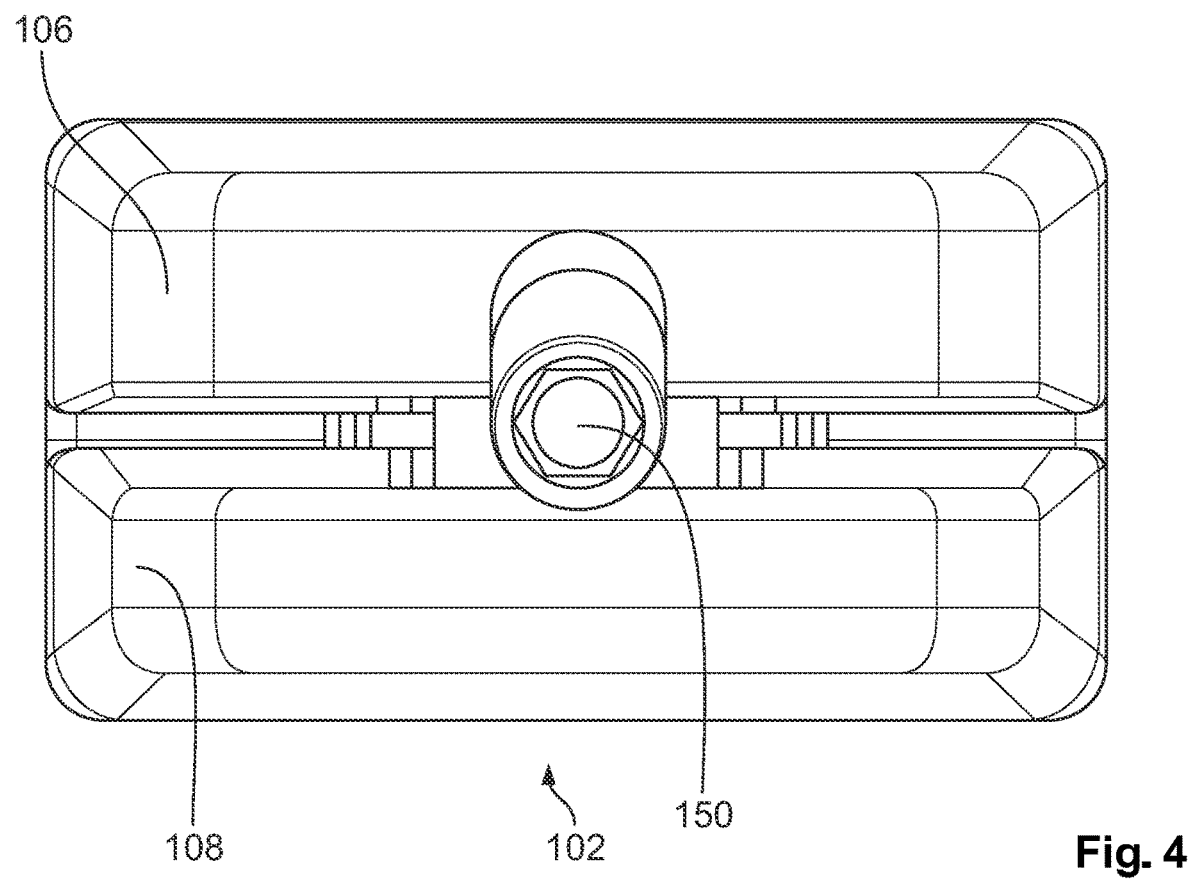
FIG. 4 is a rear view of the implant of FIG. 1.

Endplates 106, 108 are connected to each other via pivot pins 116. As shown, pivot pins 116 are dowel pins inserted substantially toward the center of the length and height of implant 100. Pivot pins 116 allow endplates 106, 108 to pivot freely relative to each other about pivot axis A-A as shown in FIG. 3. Upon insertion of implant 100 into the intervertebral space, this permits endplates 106, 108 to naturally conform to the tapered angle between two adjacent vertebrae and maximize endplate contact therewith. Although shown as two simple dowels, it is contemplated to utilize a single axle or structures such as bearings or the like to facilitate an even smoother pivoting of the end plates. A further embodiment may include a single ball bearing housed between the endplates to permit pivoting about a longitudinal axis as well as a lateral axis. Additionally, it is contemplated to provide ratcheting pins that permit movement of the end plates in one direction, but prevent it in another direction.

Figure 6A:
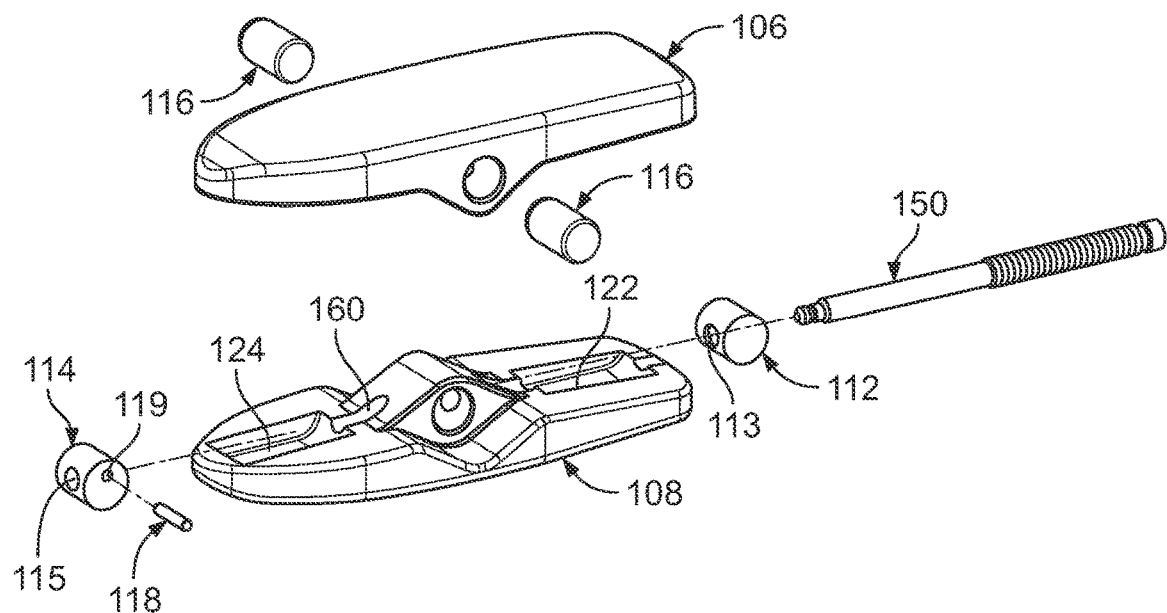
FIG. 6A is an exploded view of the implant of FIG. 1.
Figure 6B:
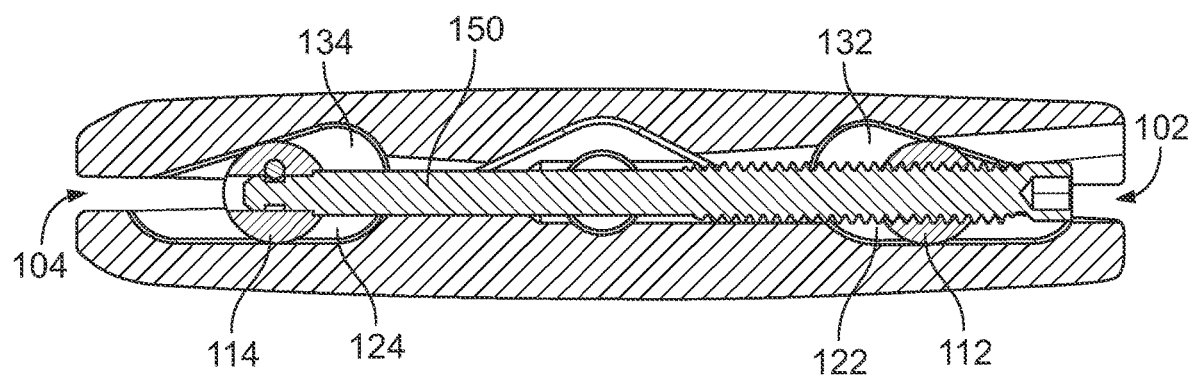
FIG. 6B is a cross-sectional side view of the implant of FIG. 1.

With reference to FIGS. 6A-6B, bottom endplate 108 has proximal groove 122 and distal groove 124 located on opposing sides of pivot pins 116, each of which includes a bottom surface that is substantially flat (i.e., parallel to the shaft) and configured to receive proximal sliding pin 112 and distal sliding pin 114, respectively. Top endplate 106 includes proximal tapered slot 132 and distal tapered slot 134 which are aligned with respective grooves 122, 124 on bottom endplate 108. The top surfaces of tapered slots 132, 134 extend at an angle transverse to the bottom surfaces of grooves 122, 124. The nature of the angled surfaces of tapered slots 132, 134 causes the space between proximal tapered slot 132 and proximal groove 122 to decrease toward proximal end 102 and the space between distal tapered slot 134 and distal groove 124 to decrease toward distal end 104, as illustrated in FIG. 6B. Such structure causes sliding pins 112, 114 to meet resistance between top and bottom endplates 106, 108 upon translation of sliding pins 112, 114, as will be discussed below in more detail. It is contemplated that the top surfaces of tapered slots 132, 134 may extend at an angle such that the space between proximal tapered slot 132 and proximal groove 122 increases toward proximal end 102 and the space between distal tapered slot 134 and distal groove 124 increases toward distal end 104. It is also contemplated that grooves 122, 124 can be identical to slots 132, 134 such that top and bottom endplates 106, 108 are mirror images of each other. Proximal sliding pin 112 is able to translate proximally and distally within proximal groove 122, while distal sliding pin 114 is able to translate proximally and distally within distal groove 124. Proximal sliding pin 112 includes proximal sliding pin bore 113 and distal sliding pin 114 includes distal sliding pin bore 115, which are configured to receive shaft 150. Shaft 150 is at least partially threaded, preferably on proximal end 102 and designed to cooperate with threaded proximal sliding pin bore 113. It is to be understood that bore 113 can be completely threaded throughout its length or only threaded along a portion thereof. It is also contemplated to utilize different structures for the cooperation between shaft 150 and bore 113, such as ratchets or the like.

Figure 7A:
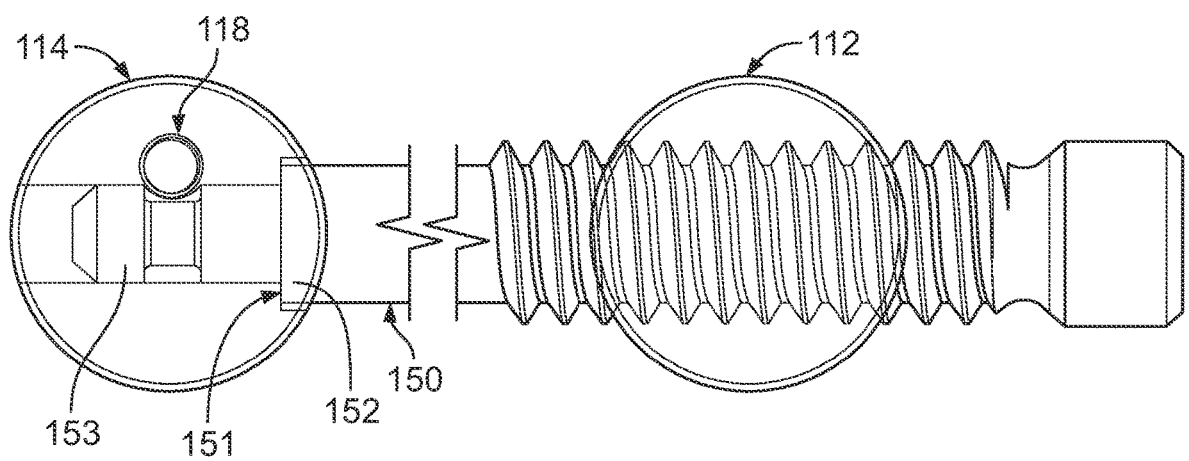
FIG. 7A is a side view of the shaft interacting with the sliding pins of the implant of FIG. 1.

In a fully assembled state, shaft 150 extends from proximal end 102 of bottom endplate 108 (a concave portion is shown at the proximal end), through proximal sliding pin bore 113 of proximal sliding pin 112, through axial hole 160 of bottom endplate 108, and finally through distal sliding pin bore 115 of distal sliding pin 114. As shown in FIG. 6A, distal sliding pin 114 further includes retainer pin bore 119 configured to receive retainer pin 118. Retainer pin bore 119 is orthogonal to and slightly offset from distal sliding pin bore 115, such that retainer pin bore 119 and distal sliding pin bore partially intersect. As illustrated in FIG. 7A, shaft 150 includes shaft shoulder 152 and shaft neck 153. Shaft neck 153 is created by cutting a circumferential groove into a segment of shaft 150 toward distal end 104 of shaft 150. Shaft shoulder 152 is created as a result of the change in diameter between shaft neck 153 and the rest of shaft 150. When implant 100 is assembled and shaft 150 is fully inserted, shaft shoulder 152 will sit flush against contact face 151 of distal sliding pin 114. Shaft neck 153 will be aligned with retainer pin 118 such that when retainer pin 118 is inserted into retainer pin bore 119 of distal sliding pin 114, retainer pin 118 prevents shaft 150 from translating longitudinally relative to distal sliding pin 114 but permits rotation of shaft 150. With shaft 150 in place as described above with respect to bottom endplate 108, top endplate 106 is positioned onto bottom endplate 108 and pivot pins 116 are pressed in on each side of implant 100. This constitutes a fully assembled implant 100.

Figure 7B:
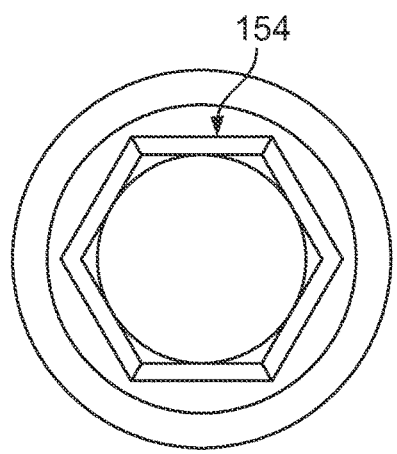
FIG. 7B is a rear view of the drive feature used to rotate the shaft of the implant of FIG. 1.

Shaft 150 can be rotated by applying torque to drive feature 154 shown in FIG. 7B. Drive feature 154 may be, but is not limited to, a female hex. Other embodiments can include any known drive features, such as a male hex for cooperating with a female hex of a drive tool. Rotation of shaft 150 results in relative movement between proximal sliding pin 112 and distal sliding pin 114 due to the threaded connection between shaft 150 and pin bore 113. In one embodiment, the distance between proximal sliding pin 112 and distal sliding pin 114 will increase when a clockwise torque is applied to drive feature 154, but decrease when a counter-clockwise torque is applied. In an alternate embodiment, the distance between proximal sliding pin 112 and distal sliding pin 114 will increase when a counter-clockwise torque is applied to drive feature 154, but decrease when a clockwise torque is applied.

Figure 8A:
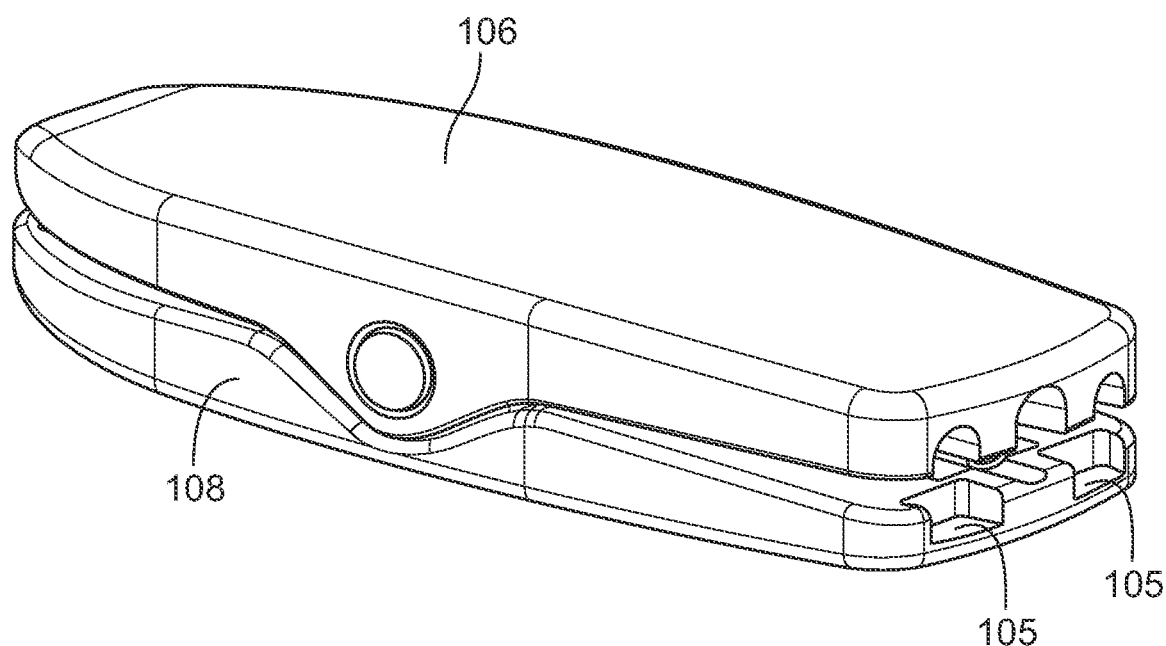
FIG. 8A is a perspective view of the implant of FIG. 1.
Figure 8B:
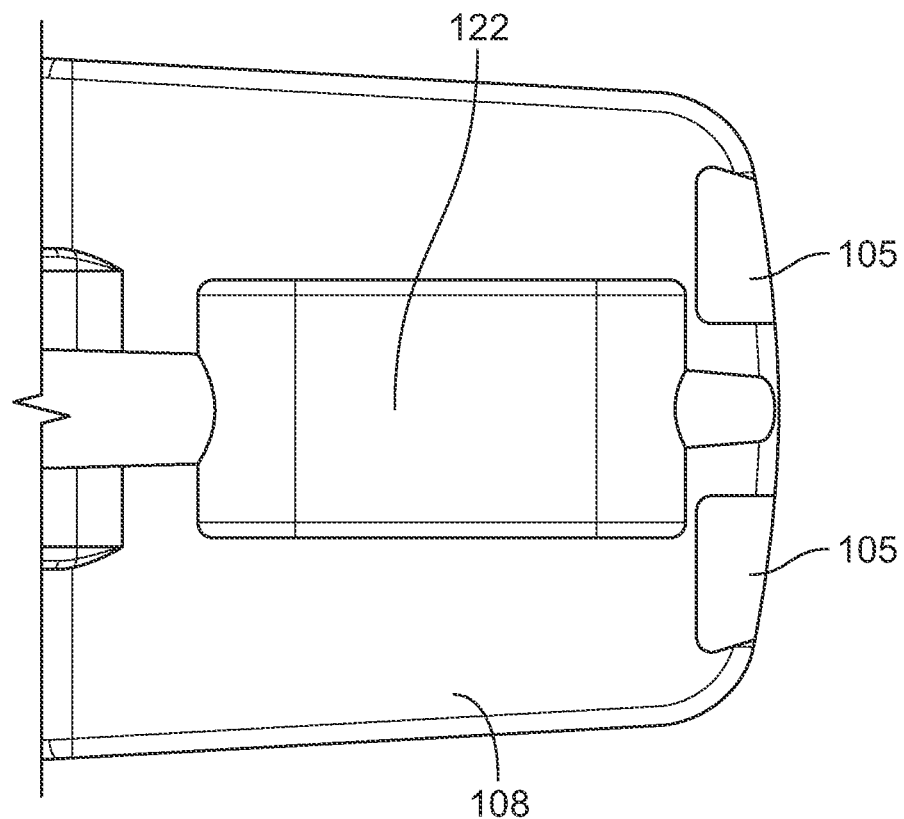
FIG. 8B is a top view of a portion of the bottom endplate of the implant of FIG. 1.

Implant 100 is configured to detachably couple to an insertion instrument for delivery into the intervertebral space. Delivery may be achieved with an insertion instrument known in the art that is capable of rigidly connecting to implant 100. As illustrated in FIGS. 8A and 8B, bottom endplate 108 includes notches 105 on proximal end 102 to allow the insertion instrument to firmly grip bottom endplate 108. Notches 105 include several surfaces for mating implant 100 with the insertion instrument. For example, a pronged insertion instrument may grip implant 100 by applying a simultaneous compressive force to the inner surface of each notch 105, or a simultaneous expansive force to the outer surface of each notch 105. Further, bottom endplate 108 may be gripped by a simultaneous pinching force on the bottom surface of notch 105 and the opposing surface of bottom endplate 108.

Once implant 100 is positioned within the disc space and any necessary corrections to the spine are made, endplates 106, 108 will pivot to conform to the natural shape of the spine. Shaft 150 is then rotated to move sliding pins 112, 114 into position to provide maximum support to endplates 106, 108 and eliminate the free pivoting motion of implant 100. When the free pivoting motion is eliminated, implant 100 is substantially locked in the resultant angular position it has taken within the disc space. In other words, the initial free pivotability of the endplates permits the implant to situate itself in an optimum position, where actuation of the shaft acts to prevent any further movements between the endplates. Additional fixation means, such as plating or a pedicle screw and/or rod constructions, may be used to stabilize implant 100 after it is fused within the disc space.

Figure 9:
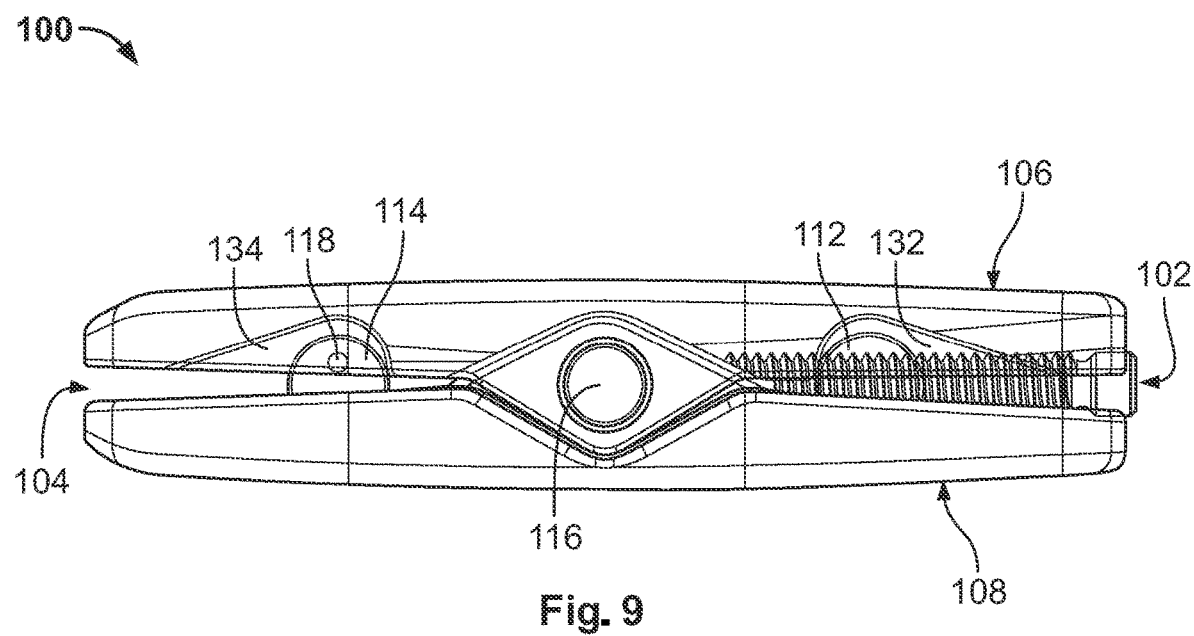
FIG. 9 is a side partial cross-sectional view of the implant of FIG. 1 in which the sliding pins are in a medial position and the endplates are freely adjustable.

FIG. 9 shows implant 100 in a free-pivoting state. Proximal sliding pin 112 and distal sliding pin 114 are located as close to pivot pins 116 as respective grooves 122, 124 will allow. Top endplate 106 includes proximal tapered slot 132 and distal tapered slot 134, allowing top endplate 106 to pivot about bottom endplate 108 without interference from sliding pins 112, 114. Implant 100 may be introduced into the intervertebral disc space in this state to allow endplates 106, 108 to adjust and find the natural angularity between vertebrae.

Figure 10:
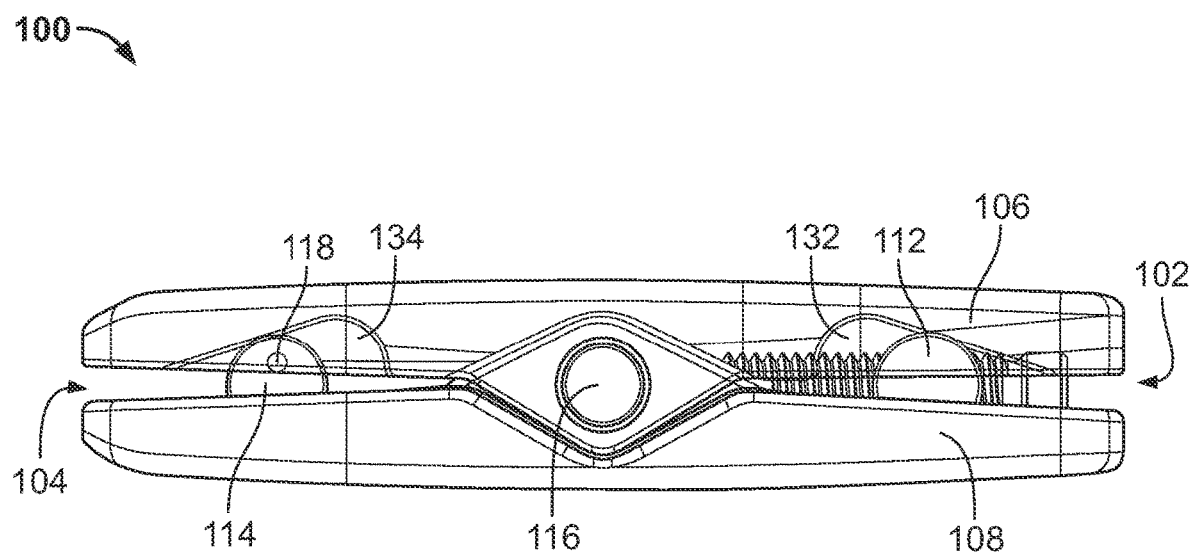
FIG. 10 is a side partial cross-sectional view of the implant of FIG. 1 in which the endplates are locked in a parallel position.

FIG. 10 shows implant 100 in an alternative position. Relative to the position of implant 100 in FIG. 9, clockwise rotation of shaft 150 has caused proximal sliding pin 112 and distal sliding pin 114 to translate longitudinally away from each other and pivot pins 116. Upon initial clockwise rotation, proximal sliding pin 112 may translate away from pivot pins 116 until it meets resistance from contact with groove 122 and tapered slot 132. After proximal sliding pin 112 meets resistance and clockwise rotation of shaft 150 continues, distal sliding pin 114 will translate away from pivot pins 116 until it meets resistance from contact with groove 124 and tapered slot 134. In an alternate embodiment, rotation of shaft 150 may cause distal sliding pin 114 to translate first until it meets resistance and continued rotation may subsequently cause proximal sliding pin 112 to translate. When both sliding pins 112, 114 reach points of resistance, sliding pins 112, 114 lock endplates 106, 108 in position and prevent any further pivoting motion. In another alternative embodiment, clockwise rotation of shaft 150 may cause sliding pins 112, 114 to simultaneously translate longitudinally away from each other until each sliding pin 112, 114 meets resistance within its respective tapered slot 132, 134.

Figure 11:
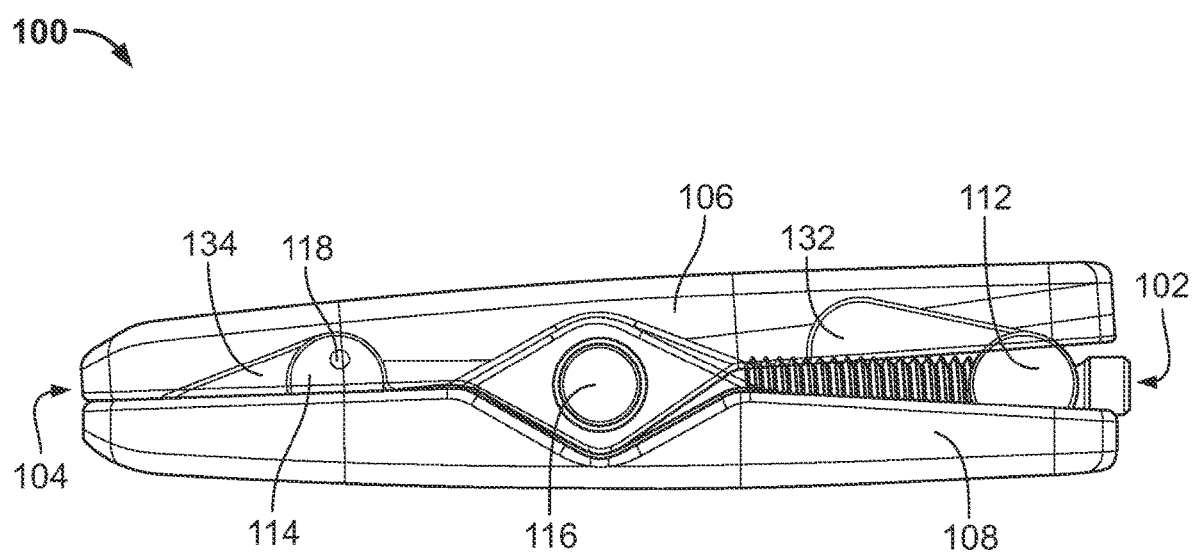
FIG. 11 is a side partial cross-sectional view of the implant of FIG. 1 in which the endplates are locked in a position of maximum angulation descending from proximal to distal end.
Figure 12:
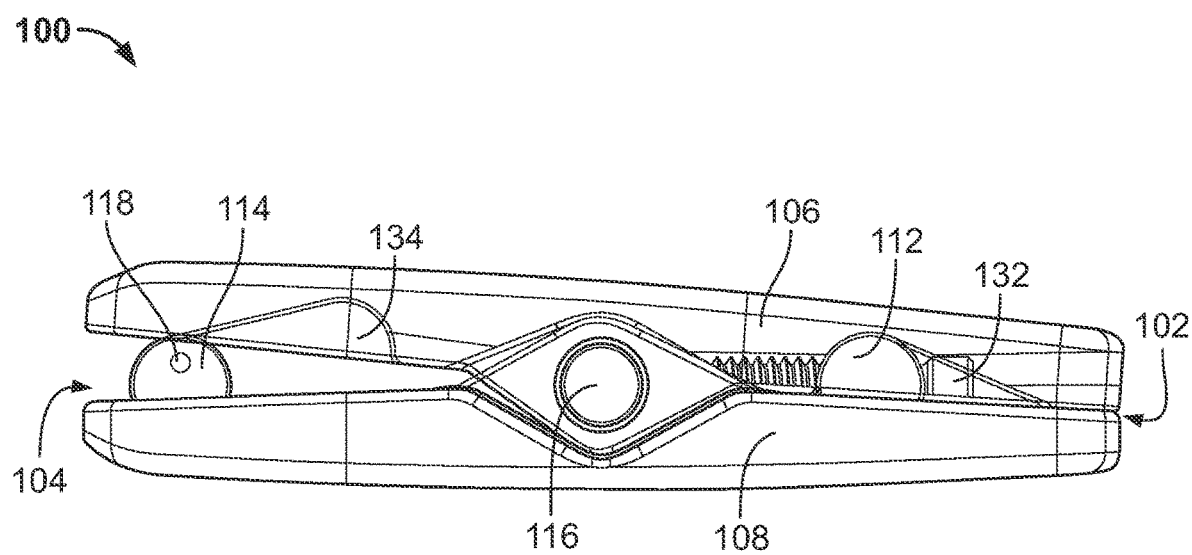
FIG. 12 is a side partial cross-sectional view of the implant of FIG. 1 in which endplates are locked in a position of maximum angulation ascending from proximal to distal end.

FIGS. 11-12 show implant 100 in the most extreme positions implant 100 is capable of assuming in the present embodiment. It is also contemplated that implant 100 can take any intermediate position between these extremes in which sliding pins 112, 114 are locked in place anywhere in the middle of respective grooves 122, 124. FIG. 11 shows implant 100 in a resulting angulation where distal end 104 is at a minimum height and proximal end 102 is at a maximum height. Implant 100 may take this position upon insertion into the intervertebral space. Upon rotation of shaft 150, distal sliding pin 114 meets immediate resistance from distal tapered slot 134, causing proximal sliding pin 112 to translate proximally. Proximal sliding pin 112 will translate proximally until it meets resistance with endplates 106, 108 and will provide support for proximal end 102 of top endplate 106 and bottom endplate 108. Implant 100 achieves a locked state when both sliding pins 112, 114 have met resistance in their respective slots 132, 134.

FIG. 12 shows implant 100 in a resulting angulation where distal end 104 is at a maximum height and proximal end 102 is at a minimum height. Implant 100 may take this position upon insertion into the intervertebral space. Upon rotation of shaft 150, proximal sliding pin 112 meets immediate resistance from proximal tapered slot 132, causing distal sliding pin 114 to translate distally. Distal sliding pin 114 will translate distally until it meets resistance with endplates 106, 108 and will provide support for distal end 104 of top endplate 106 and bottom endplate 108. Implant 100 achieves a locked state when both sliding pins 112, 114 have met resistance in their respective slots 132, 134.

Figure 5:
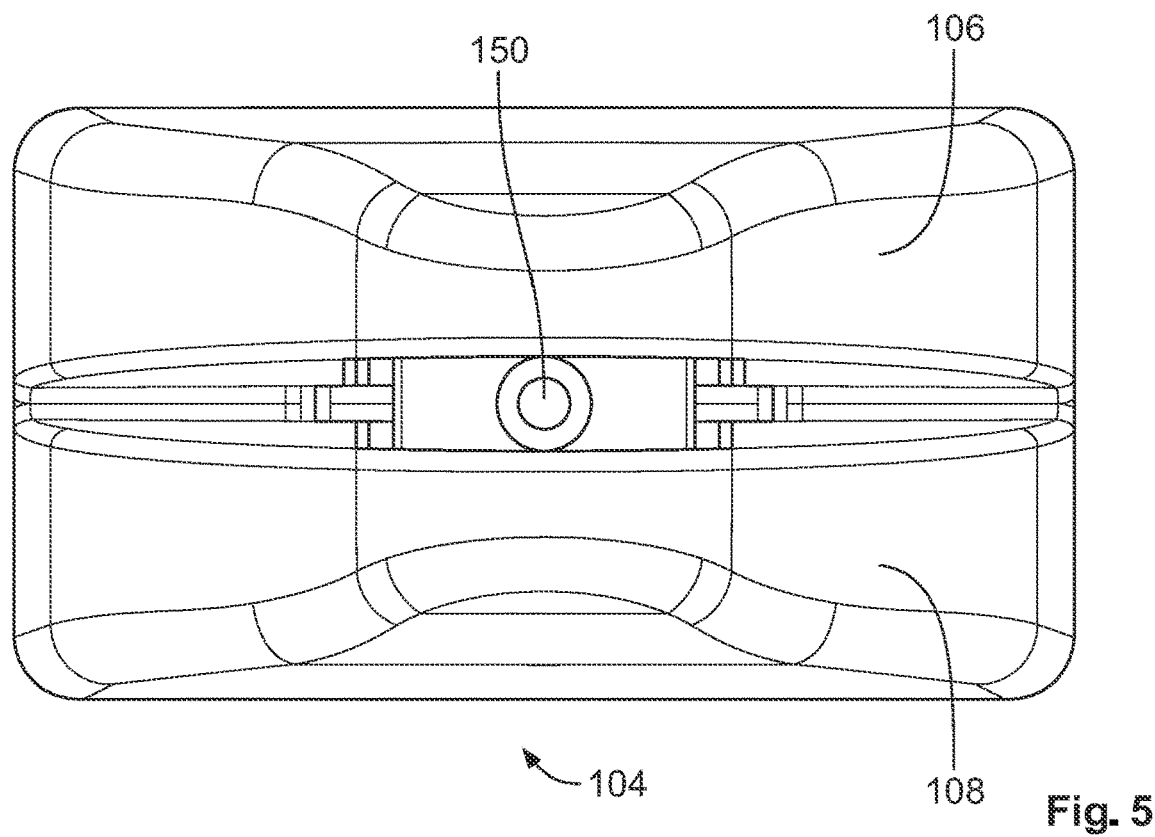
FIG. 5 is a front view of the implant of FIG. 1.
Figure 13:
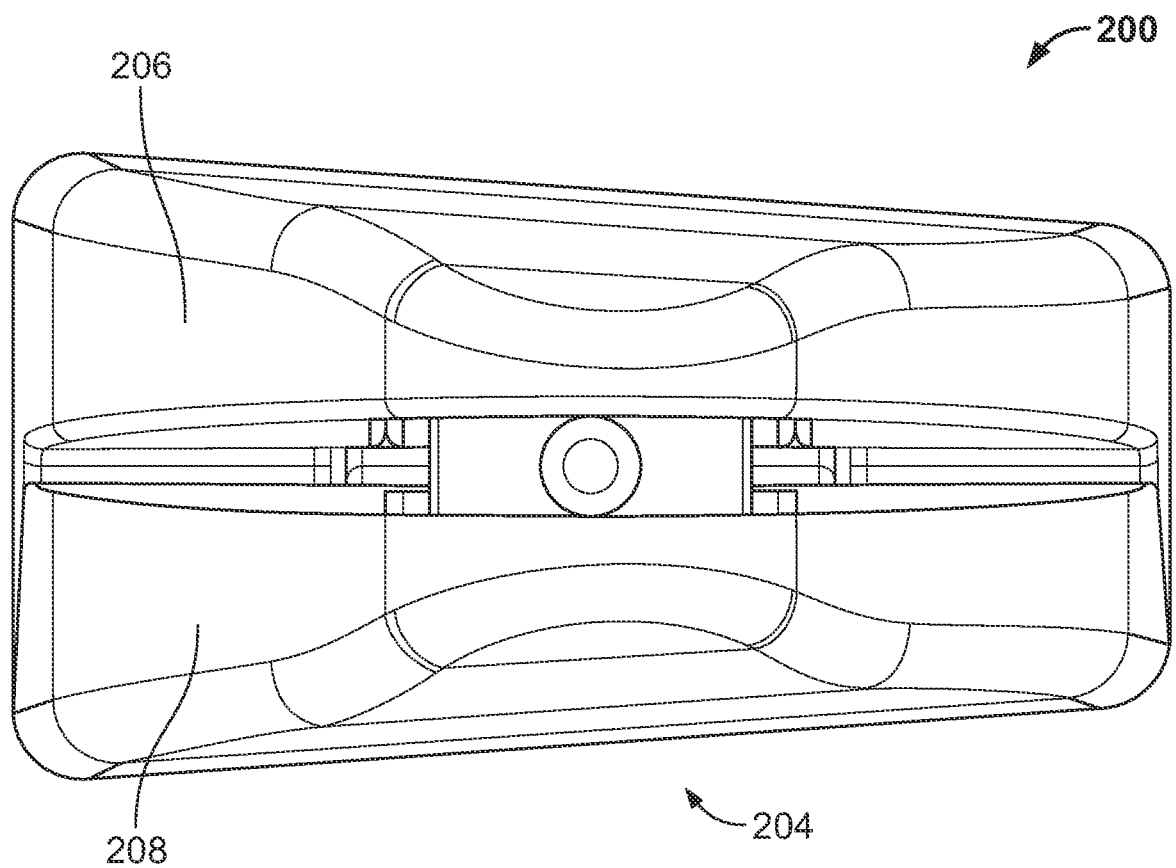
FIG. 13 is a front view of an implant according to another embodiment of the present invention.

When viewing implant 100 from distal end 104 as shown in FIG. 5, top endplate 106 and bottom endplate 108 lie in planes parallel to each other. This embodiment would preferably be used for patients with spines having a normal curvature. Spines having excess curvature may be lordotic, which is an increased inward curve of the lumbar spine, or kyphotic, which is an increased outward curve of the thoracic spine. FIG. 13 shows an alternate embodiment of implant 200 which can be used to treat a lordotic spine. FIG. 13 shows a front view of distal end 204, in which height of implant 200 varies from one lateral side to the other, causing top and bottom endplates 206, 208 to lie in planes that would intersect. Such a configuration of implant 200 accommodates the additional curvature of a lordotic spine to allow for insertion into the intervertebral space and create optimal contact between endplates 206, 208 and the vertebral bodies. It is also contemplated that the mirror image of implant 200 shown in FIG. 13 can be used to treat a kyphotic spine.

Figure 14A:
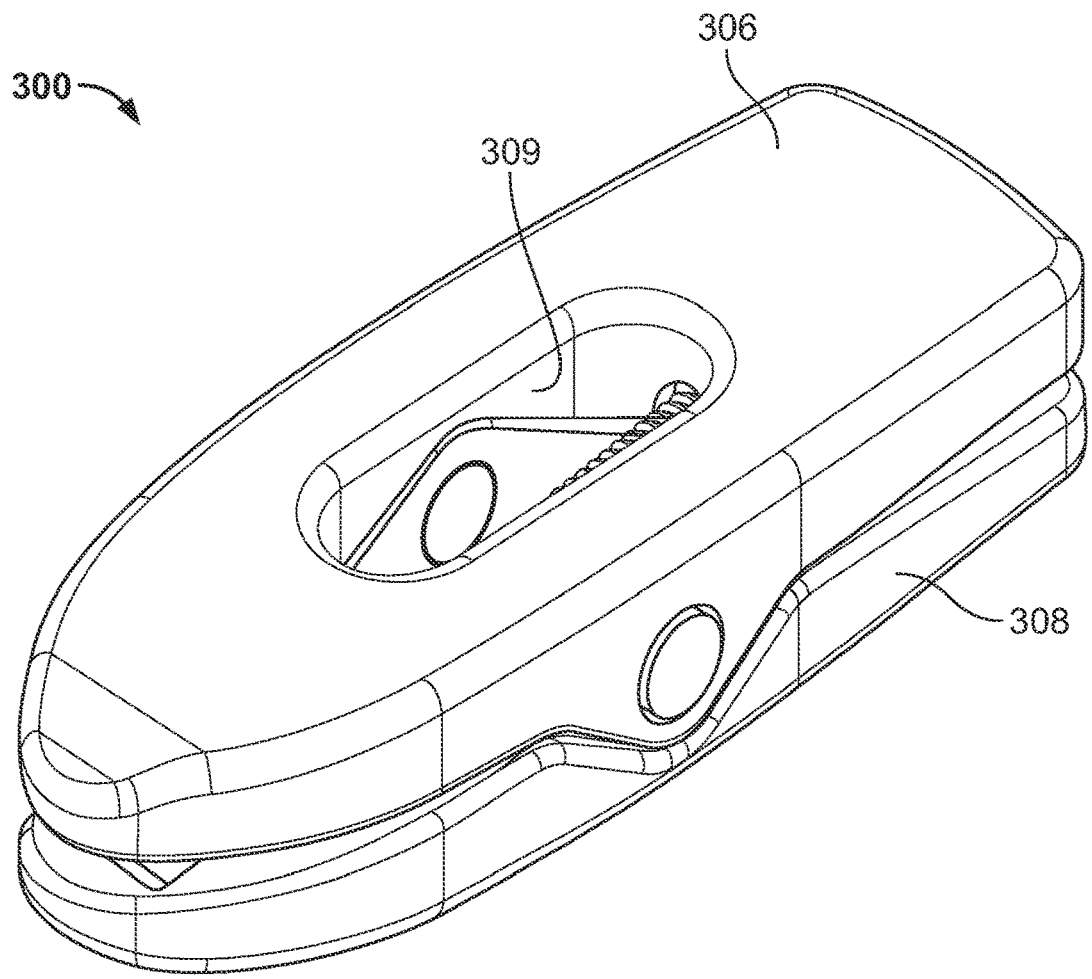
FIG. 14A is a perspective view of an alternate embodiment of an implant having a graft window in the top endplate.
Figure 14B:
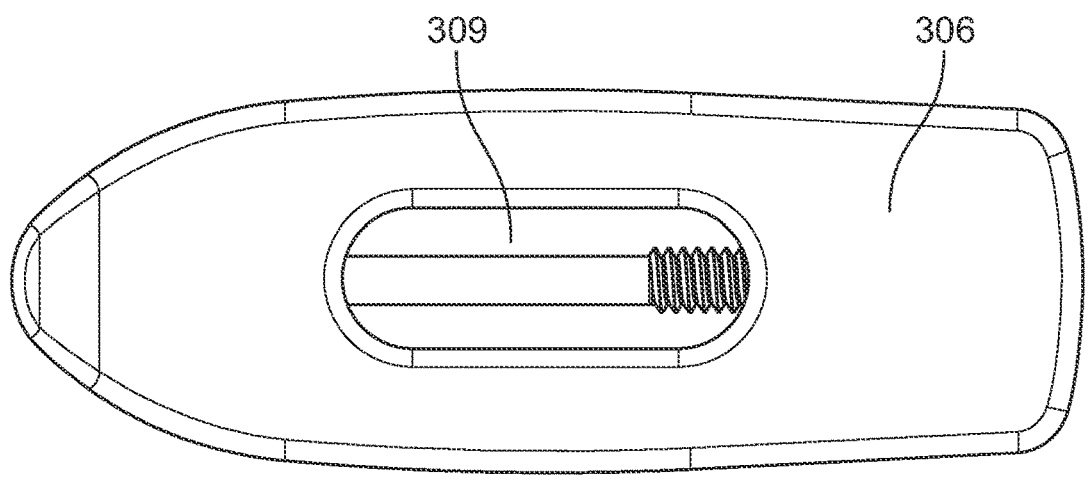
FIG. 14B is a top view of the implant of FIG. 14A.

FIGS. 14A-14B illustrate an alternate embodiment of implant 300 including a graft window 309 in top endplate 306. Graft window 309 is a stadium-shaped bore that allows for access to the space between top endplate 306 and bottom endplate 308 after implant 300 has been fully assembled. The access permitted by graft window 309 can be used to inject bone graft material into the inside of implant 300 to promote placement and stabilization of implant between vertebral bodies.

While the present embodiment has an intended use for spinal fusion, the design can be used in any context which requires leveling or providing support between two adjacent surfaces. The implant may further be introduced into the intervertebral space through the anterior or posterior of the spine. It is further contemplated that endplates need not be flat plates, but can take on any size and shape necessary to conform and fit to a surface, such as a U-shape. Endplates may also include means for enhancing grip to surfaces, such as an adhesive, high-friction rubber, or a ridged surface. In addition to titanium or steel, the device and its components may be manufactured of a polyether ether ketone (PEEK) material. All components may be manufactured of the same material or different materials. For instance, the endplates may be manufactured from PEEK, whereas sliding pins and shaft may be manufactured from a metal.

In an alternate embodiment, the shaft may need not be rotated to actuate, but may translate with a push from the proximal end by a user or a tool. The shaft may be capable of actuation from both ends to allow for placement of the implant in either direction. The shaft may include beads spaced along its length, and the endplates may internally include a clip such as a butterfly clasp that closes due to compression of the implant from the weight of adjacent surfaces, and the implant may be locked upon actuation of the beaded shaft through the clasp. The sliding pins can take on any shape, including a triangular shape to match the grooves between the endplates. Pivot pins may include teeth or ridges around their circumferences and endplates may be configured to receive teeth or ridges of pivot pins to dampen pivotability and stabilize the endplates while shaft is being actuated.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An intervertebral implant comprising:
a first endplate;
a second endplate pivotally coupled to the first endplate by a pivot pin;
a first sliding pin slidably disposed between the first and second endplates and on a first side of the pivot pin;
a second sliding pin disposed on a second side of the pivot pin opposite the first side; and
a shaft extending at least partially through the first sliding pin,
wherein actuation of the shaft locks the first and second endplates with respect to each other.

2. The implant of claim 1, wherein the first endplate defines a bore in which the shaft extends therethrough.

3. The implant of claim 1, wherein the first endplate defines a first groove configured to receive the first sliding pin.

4. The implant of claim 1, wherein the first sliding pin defines a threaded bore configured to receive the shaft.

5. The implant of claim 3, further comprising a second sliding pin slidably disposed between the first and second endplate, wherein the first sliding pin is adjacent a first end of the implant and the second sliding pin is adjacent a second end of the implant.

6. The implant of claim 5, wherein the first endplate defines a second groove configured to receive the second sliding pin, the second sliding pin defining a bore configured to receive the shaft.

7. The implant of claim 5, wherein the second endplate defines a first tapered slot configured to receive the first sliding pin, and the second endplate further defines a second tapered slot configured to receive the second sliding pin.

8. The implant of claim 5, wherein the second sliding pin further defines a hole configured to receive a locking pin that extends through the second sliding pin and within a circumferential indentation in the shaft to prevent the shaft from translating relative to the second sliding pin but allowing rotation of the shaft.

9. The implant of claim 5, wherein a clockwise rotation of the shaft causes the first sliding pin to translate along the shaft axis in a direction away from the second sliding pin.

10. The implant of claim 1, wherein the first and second endplates are pivotally coupled by at least one pivot pin.

11. The implant of claim 10, wherein the pivot pin is located at a center of the implant and extends orthogonal to a longitudinal axis of the implant.

12. The implant of claim 1, wherein the first endplate lies in a first plane and the second endplate lies in a second plane parallel to the first plane.

13. The implant of claim 1, wherein the first endplate lies in a first plane and the second endplate lies in a second plane that intersects with the first plane.

14. The implant of claim 1, wherein the shaft is at least partially threaded.

15. The implant of claim 1, wherein the shaft has a drive feature configured to receive a tool for rotating the shaft.

16. The implant of claim 1, wherein the first and second endplates have bullet-shaped ends.

17. A method of positioning an interbody fusion device, the method comprising:
inserting an implant between first and second vertebral bodies, the implant including a first endplate for contacting the first vertebral body and a second endplate for contacting the second vertebral body;

allowing the first and second endplates to freely pivot about a pivot pin with respect to each other to conform to the angle between the two adjacent vertebrae; and actuating a shaft of the implant to translate first and second sliding pins to lock the first and second endplates with respect to each other.

18. The method of claim 17, wherein the actuating step includes translating the first and second sliding pin until the first and second sliding pins meet resistance between the first and second endplates.

19. The method of claim 18, wherein during the inserting step, the first and second sliding pins are positioned medially to allow the implant to pivot into the natural state of the vertebrae.

20. An intervertebral implant comprising:
a first endplate extending along a longitudinal axis, the first endplate defining a groove;
a second endplate pivotally coupled to the first endplate by a pivot pin, the second endplate defining a tapered slot aligned with the groove along the longitudinal axis;
a first sliding pin slidably disposed within the groove and the tapered slot on a first side of the pivot pin; and
a second sliding pin disposed on a second side of the pivot pin opposite the first side,
wherein movement of the sliding pin along the longitudinal axis is configured to pivot the second endplate relative to the first endplate.

\* \* \* \* \*